United States Patent
Takayama

(10) Patent No.: US 9,226,716 B2
(45) Date of Patent: Jan. 5, 2016

(54) NUCLEAR MEDICINE IMAGING APPARATUS AND RADIATION THERAPY APPARATUS

(75) Inventor: Takuzo Takayama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 546 days.

(21) Appl. No.: 13/152,658

(22) Filed: Jun. 3, 2011

(65) Prior Publication Data

US 2011/0297833 A1 Dec. 8, 2011

(30) Foreign Application Priority Data

Jun. 3, 2010 (JP) ................... 2010-128226

(51) Int. Cl.
*G01T 1/161* (2006.01)
*A61B 6/03* (2006.01)
(52) U.S. Cl.
CPC ..................... *A61B 6/037* (2013.01)
(58) Field of Classification Search
USPC .................................. 250/363.04
See application file for complete search history.

(56) References Cited

U.S. PATENT DOCUMENTS

| 4,559,597 | A * | 12/1985 | Mullani | 600/407 |
| 2005/0253074 | A1* | 11/2005 | Jones et al. | 250/363.04 |
| 2008/0135764 | A1* | 6/2008 | Braess | 250/354.1 |
| 2009/0324042 | A1 | 12/2009 | Laurence et al. | |

FOREIGN PATENT DOCUMENTS

| JP | 2007-037781 | 2/2007 |
| JP | 2007-155431 | 6/2007 |
| JP | 2008-125884 | 6/2008 |
| JP | 2009-544944 | 12/2009 |
| WO | WO 2010143082 A1 * | 12/2010 |

OTHER PUBLICATIONS

Japan Industries Association of Radiological Systems, "Medical Image/Radiological Equipment Hand Book", published by Nago Bijutsu Insatsu Kabushiki Kaisha, 2001, Partial English Translation, 5 pages.
Office Action issued Jun. 25, 2014 in Japanese Patent Application No. 2010-128226 (with English translation).

* cited by examiner

*Primary Examiner* — David Porta
*Assistant Examiner* — Shun Lee
(74) *Attorney, Agent, or Firm* — Oblon, McClelland, Maier & Neustadt, L.L.P.

(57) ABSTRACT

A nuclear medicine imaging apparatus according to an embodiment includes a gradation width storage, an estimating unit, and an image generating unit. The gradation width storage is configured to store the gradation width of an image determined by the temporal resolution of a detector. The estimating unit is configured to estimate the spatial position of a positron on the basis of the spatial position of a set of detectors and a set of detection times. The image generating unit is configured to allocate pixel value to pixels corresponding to the gradation width around the estimated spatial position such that a spatial resolution corresponding to the temporal resolution is reflected on a line linking the set of detectors, thereby generating an image.

9 Claims, 9 Drawing Sheets

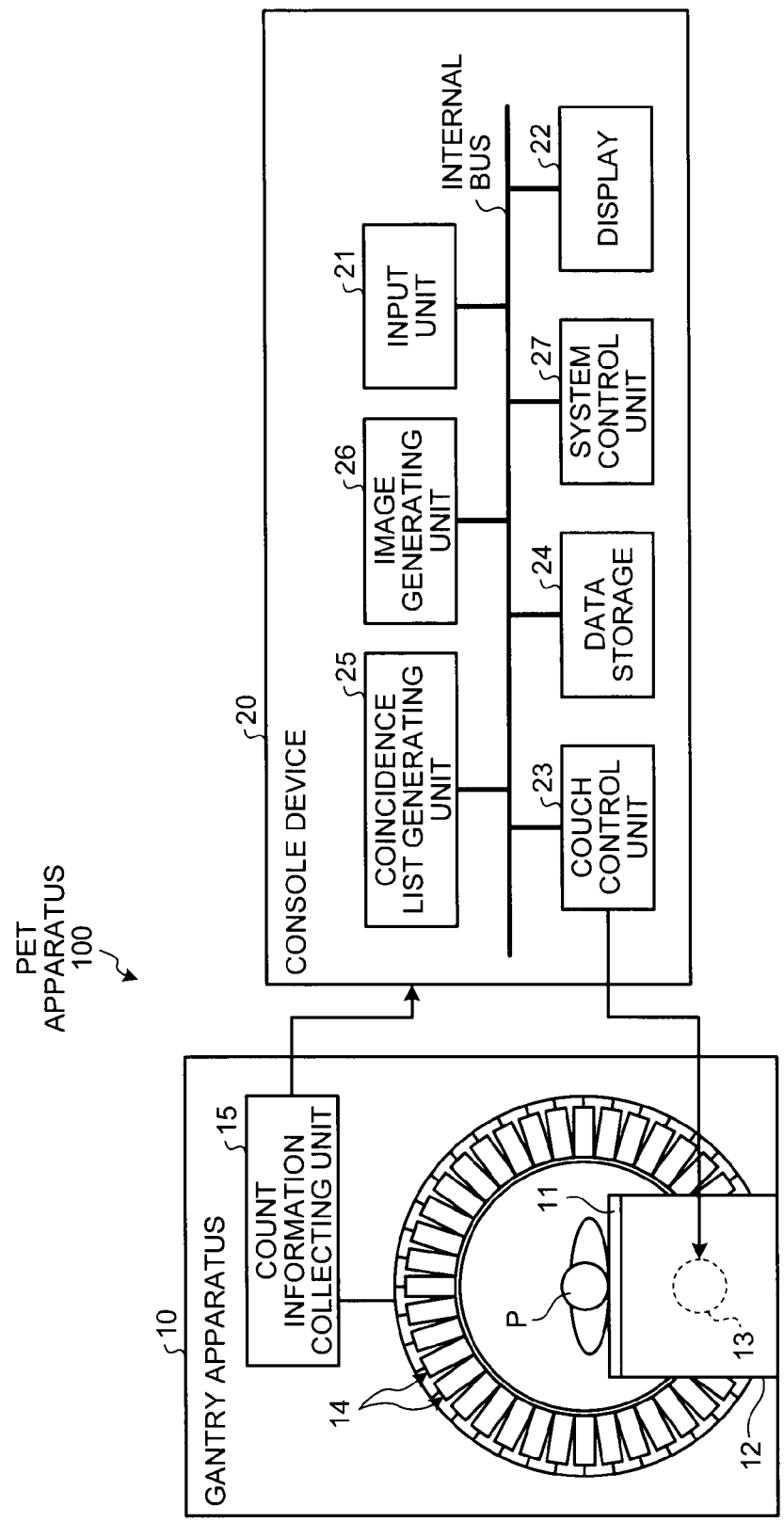

| MODULE ID | SCINTILLATOR NO. (P) | ENERGY VALUE (E) | DETECTION TIME (T) |
|---|---|---|---|
| D1 | P11 | E11 | T11 |
|  | P12 | E12 | T12 |
|  | P13 | E13 | T13 |
|  | ⋮ | ⋮ | ⋮ |

| MODULE ID | SCINTILLATOR NO. (P) | ENERGY VALUE (E) | DETECTION TIME (T) |
|---|---|---|---|
| D2 | P21 | E21 | T21 |
|  | P22 | E22 | T22 |
|  | P23 | E23 | T23 |
|  | ⋮ | ⋮ | ⋮ |

| MODULE ID | SCINTILLATOR NO. (P) | ENERGY VALUE (E) | DETECTION TIME (T) |
|---|---|---|---|
| D3 | P31 | E31 | T31 |
|  | P32 | E32 | T32 |
|  | P33 | E33 | T33 |
|  | ⋮ | ⋮ | ⋮ |

| COINCIDENCE NO. | SCINTILLATOR NO. (P) | ENERGY VALUE (E) | DETECTION TIME (T) | SCINTILLATOR NO. (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

FIG.6

| COUNT NO. | SPATIAL POSITION | DETECTION TIME |
|---|---|---|
| 1 | (x1, y1, z1) | t1 |
| 2 | (x2, y2, z2) | t2 |
| 3 | (x3, y3, z3) | t3 |
| ⋮ | ⋮ | ⋮ |
| n | (xn, yn, zn) | tn |

FIG.7

| TEMPORAL RESOLUTION (FWHM) | GRADATION WIDTH (FWHM) |
|---|---|
| ⋮ | ⋮ |
| 100 PICO SECONDS | 30 mm |
| 150 PICO SECONDS | 45 mm |
| 200 PICO SECONDS | 60 mm |
| ⋮ | ⋮ |

FWHM

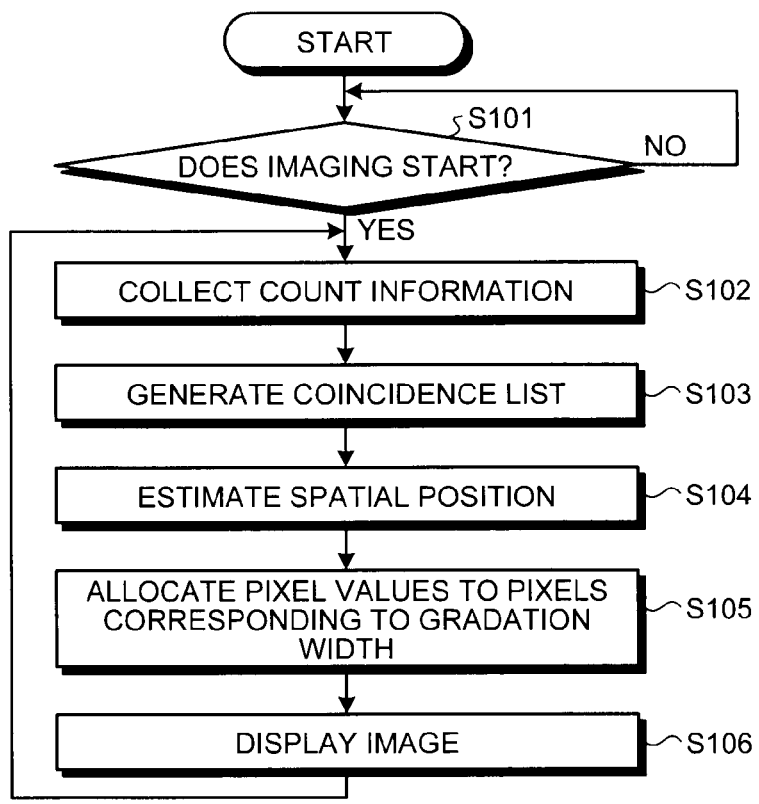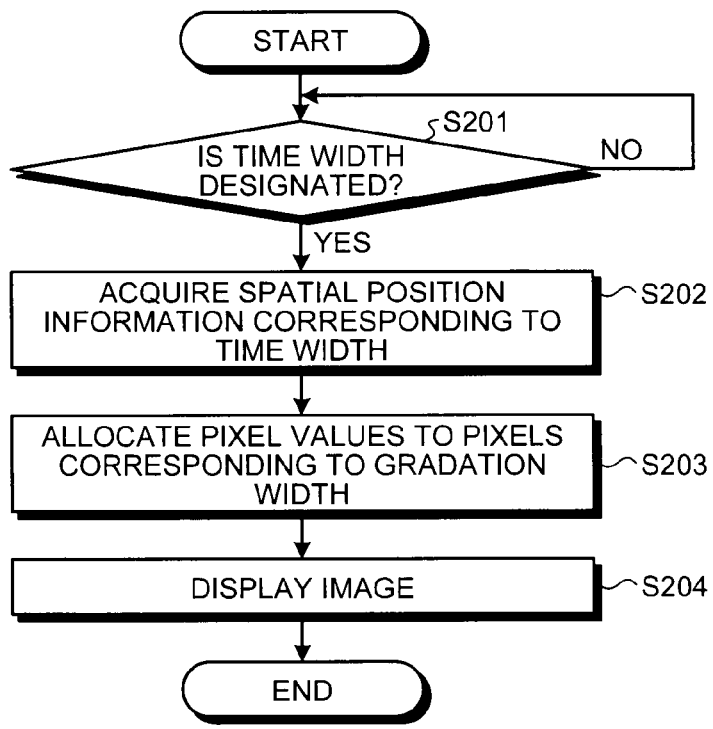

NUCLEAR MEDICINE IMAGING APPARATUS AND RADIATION THERAPY APPARATUS

CROSS-REFERENCE TO RELATED APPLICATIONS

This application is based upon and claims the benefit of priority from Japanese Patent Application No. 2010-128226, filed on Jun. 3, 2010, the entire contents of all of which are incorporated herein by reference.

FIELD

Embodiments described herein relate generally to a nuclear medicine imaging apparatus and a radiation therapy apparatus.

BACKGROUND

In recent years, as a nuclear medicine imaging apparatus, a positron emission computed tomography apparatus (hereinafter, referred to as a PET apparatus) has been known. The PET apparatus generates, for example, the functional image of body tissues. Specifically, in the imaging operation of the PET apparatus, first, a medicine including positron emitting nuclides is given to the subject. Then, the positron emitting nuclides that are selectively introduced into the body tissues of the subject emit positrons and the emitted positrons are coupled to electrons and are then extinguished. In this case, the positron emits a pair of gamma rays substantially in the opposite direction. The PET apparatus detects the gamma rays using detectors that are arrange in a ring shape around the subject and generates a coincidence list from the detection result. Then, the PET apparatus performs reconstruction using a back projection process on the basis of the generated coincidence list, thereby generating a PET image.

In recent years, a PET apparatus having a time of flight (TOF) function has appeared. A PET apparatus that does not have the TOF function performs reconstruction on the assumption that the positrons are present with equal probability on a line of response (LOR) linking a set of detectors that detect a pair of gamma rays. In contrast, the PET apparatus having the TOF function calculates the spatial position of the positron on the LOR using the difference between the detection times when the set of detectors detect the gamma rays. The PET apparatus having the TOF function adds the calculated spatial position and performs reconstruction using the back projection process, thereby generating a PET image.

However, in the related art, it takes a long time to reconstruct an image using the back projection process. As a result, it takes a long time to generate a PET image. For example, in the related art, it takes a few minutes to generate the PET image after the image operation is performed by the PET apparatus. Therefore, it is necessary to reduce the time required to generate the PET image.

BRIEF DESCRIPTION OF THE DRAWINGS

FIG. 1 is a block diagram illustrating the structure of a PET apparatus according to a first embodiment;

FIG. 5 is a diagram illustrating an example of a coincidence list stored in a coincidence list storage according to the first embodiment;

FIG. 6 is a diagram illustrating an example of spatial position information stored in a spatial position information storage according to the first embodiment;

FIG. 7 is a diagram illustrating an example of the gradation width of an image stored in a gradation width storage according to the first embodiment;

FIG. 12 is a flowchart illustrating a process of displaying the PET image in real time;

FIG. 13 is a flowchart illustrating a process of displaying the PET image after an imaging operation.

DETAILED DESCRIPTION

Figure 2A:
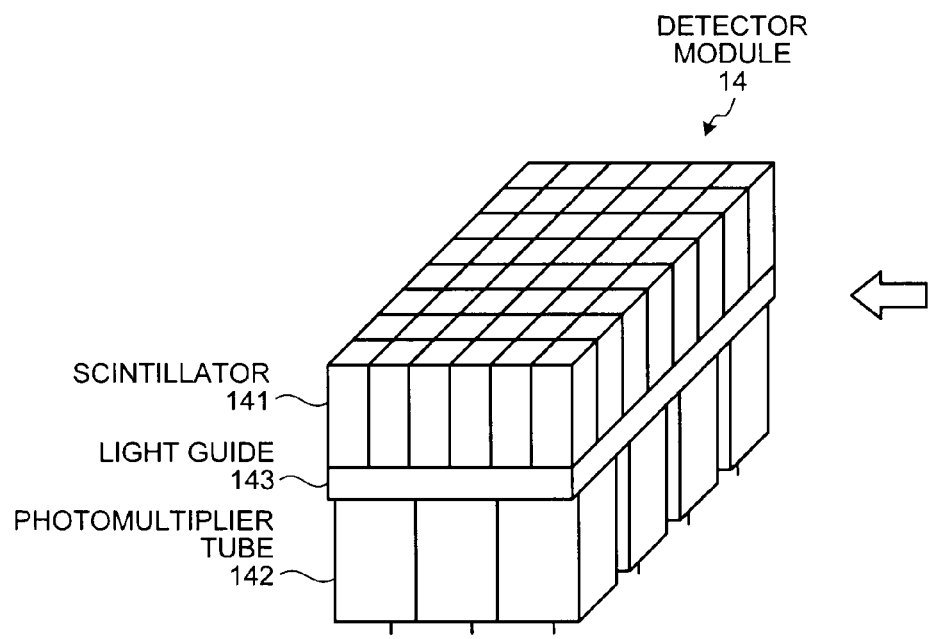
FIG. 2A is a diagram illustrating a detector module according to the first embodiment.

The nuclear medicine imaging apparatus according to the present embodiments includes a gradation width storage, an estimating unit, and an image generating unit. The gradation width storage is configured to store a gradation width of an image determined by the temporal resolution of a detector which detects radiation. The estimating unit is configured to estimate the spatial position of a positron on a line linking a set of detectors which detect a pair of radiations emitted from the positron, on the basis of the spatial position of the set of detectors and a set of detection times when the set of detectors detect the pair of radiations. The image generating unit is configured to allocate pixel values to pixels corresponding to the gradation width which is stored in the gradation width storage around the spatial position estimated by the estimating unit such that a spatial resolution corresponding to the temporal resolution is reflected on the line linking the set of detectors, thereby generating an image.

Hereinafter, a PET apparatus 100 according to a first embodiment will be described as an example of a nuclear medicine imaging apparatus and a radiation therapy apparatus according to embodiments.

The PET apparatus 100 according to the first embodiment does not generate a PET image with reconstruction using a back projection process, but generates a PET image by allocating pixel values to pixels corresponding to a gradation width, which is determined by the temporal resolution of a detector, around the spatial position of the positron estimated on a line of response (LOR). In this way, according to the PET apparatus 100 of the first embodiment, it is possible to reduce the time required to generate the PET image and display the PET image in real time during an imaging operation. This function is implemented by the process of an image generating unit 26, which will be described below.

Next, the structure of the PET apparatus 100 according to the first embodiment will be described with reference to FIGS. 1 to 11. FIG. 1 is a block diagram illustrating the structure of the PET apparatus 100 according to the first embodiment. As shown in FIG. 1, the PET apparatus 100 according to the first embodiment includes a gantry 10 and a console 20.

The gantry 10 detects a pair of gamma rays emitted from a positron and collects count information on the basis of the detection result. As shown in FIG. 1, the gantry 10 includes a top plate 11, a couch 12, a couch driving unit 13, a detector module 14, and a count information collecting unit 15. As shown in FIG. 1, the gantry 10 includes a cavity serving as an imaging hole.

The top plate 11 is a bed on which a subject P lies and is provided on the couch 12. The couch driving unit 13 moves the couch 12 under the control of a couch control unit 23, which will be described below. For example, the couch driving unit 13 moves the couch 12 to move the subject P into the imaging hole of the gantry 10.

The detector module 14 detects gamma rays emitted from the subject P. As shown in FIG. 1, a plurality of detector modules 14 is arranged in the gantry 10 so as to surround the subject P in a ring shape.

Figure 2B:
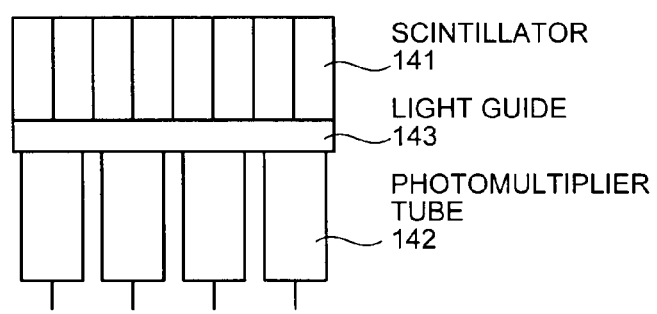
FIG. 2B is a diagram illustrating the detector module according to the first embodiment.

FIGS. 2A and 2B are diagrams illustrating the detector module 14 according to the first embodiment. As shown in FIG. 2A, the detector module 14 is a photon-counting and anger-type detector and includes scintillators 141, photomultiplier tubes (PMTs) 142, and a light guide 143. FIG. 2B shows the detector module 14, as viewed from the direction of an arrow shown in FIG. 2A.

The scintillator 141 converts the gamma ray that has been emitted from the subject P and then incident into visible light and outputs the converted visible light (hereinafter, referred to as scintillation light). The scintillators 141 are made of a scintillator crystal, such as sodium iodide (NaI) or bismuth germanate (BGO), and are two-dimensionally arranged as shown in FIG. 2A. The photomultiplier tube 142 multiplies the scintillation light output from the scintillator 141 and converts the scintillation light into an electric signal. As shown in FIG. 2A, a plurality of photomultiplier tubes 142 is arranged. The light guide 143 transmits the scintillation light output from the scintillators 141 to the photomultiplier tubes 142. The light guide 143 is made of, for example, a plastic material having high light transmittance.

The photomultiplier tube 142 includes a photocathode that receives the scintillation light and generates photoelectrons, a multi-stage dynode that generates an electric field for accelerating the generated photoelectrons, and an anode which is an outlet through which electrons flow out. The electron emitted from the photocathode by the photoelectric effect is accelerated to the dynode and collides with the surface of the dynode. As a result, a plurality of electrons is ejected from the surface of the dynode. This phenomenon is repeated over the multi-stage dynode and the number of electrons increases by geometrical progression. As a result, the number of electrons in the anode increases to about 1,000,000. In this example, the gain of the photomultiplier tube 142 is 1,000,000. In addition, a voltage of 1000 V (volt) or more is generally applied between the dynode and the anode in order to perform amplification using the avalanche phenomenon.

As such, in the detector module 14, the scintillator 141 converts the gamma ray emitted from the subject P into scintillation light and the photomultiplier tube 142 converts the converted scintillation light into an electric signal. In this way, the detector module 14 detects the gamma ray emitted from the subject P.

Returning to FIG. 1, the count information collecting unit 15 collects count information on the basis of the detection result of the detector module 14. Specifically, the count information collecting unit 15 collects the detection position of the gamma ray incident on the detector module 14, the energy value of the gamma ray at the time when the gamma ray is incident on the detector module 14, and the detection time of the gamma ray incident on the detector module 14 for each detector module 14 and transmits the collected count information to the console 20.

First, the count information collecting unit 15 performs an anger-type position calculating process in order to collect the detection position from the detection result of the detector module 14. Specifically, the count information collecting unit 15 specifies the photomultiplier tubes 142 that convert the scintillation light emitted from the scintillators 141 into electric signals at the same timing. Then, the count information collecting unit 15 calculates the center position using the position of each of the specified photomultiplier tubes 142 and the energy value of the gamma ray corresponding to the intensity of the electric signals, thereby determining a scintillator number (P) indicating the position of the scintillator 141 on which the gamma ray is incident. When the photomultiplier tube 142 is a position-detection-type photomultiplier tube, the photomultiplier tube 142 may collect the detection position.

The count information collecting unit 15 integrates the electric signal output from each photomultiplier tube 142 to determine the energy value (E) of the gamma ray incident on the detector module 14. In addition, the count information collecting unit 15 collects the detection time (T) when the detector module 14 detects the gamma ray. For example, the count information collecting unit 15 collects the detection time (T) with an accuracy of $10^{-12}$ seconds (picoseconds). The detection time (T) may be absolute time or the time elapsed from, for example, the start of image capture.

As such, the count information collecting unit 15 collects, as count information, the scintillator number (P), the energy value (E), and the detection time (T).

The PET apparatus 100 according to the first embodiment generates a PET image in real time and displays the generated PET image in real time during the capture of the PET image, which will be described below. Therefore, whenever collecting the count information during an imaging operation, the count information collecting unit 15 instantly transmits the collected count information to the console 20.

When the operator operates the PET apparatus 100, the console 20 controls the capture of the PET image and generates the PET image using the count information collected by the gantry 10. Specifically, as shown in FIG. 1, the console 20 includes an input unit 21, a display 22, a couch control unit 23, a data storage 24, a coincidence list generating unit 25, an image generating unit 26, and a system control unit 27. The units of the console 20 are connected to each other through an internal bus.

The input unit 21 includes, for example, a mouse or a keyboard that is used by the operator of the PET apparatus 100 to input various kinds of instructions or various kinds of setting and transmits the input various kinds of instructions or various kinds of setting to the system control unit 27. The display 22 is, for example, a monitor that is referred to by the operator and displays the PET image or a graphical user interface (GUI) for receiving various kinds of instructions or various kinds of setting from the operator under the control of the system control unit 27. The couch control unit 23 controls the couch driving unit 13.

Figures 3, 4:
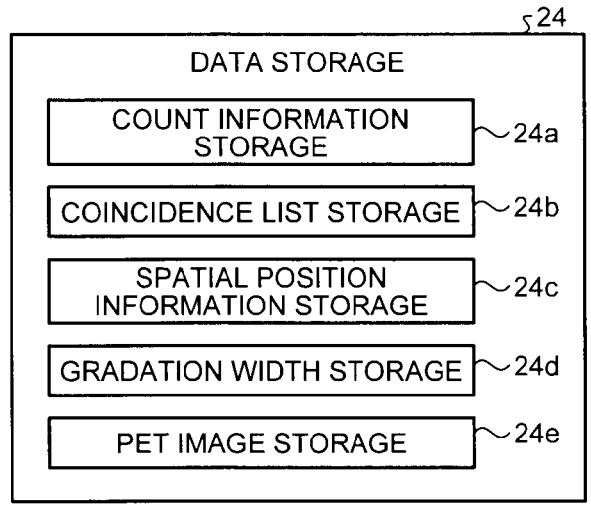
FIG. 3 is a diagram illustrating a data storage according to the first embodiment.
FIG. 4 is a diagram illustrating an example of count information stored in a count information storage according to the first embodiment.

The data storage 24 stores various kinds of data used in the PET apparatus 100. FIG. 3 is a diagram illustrating the data storage 24 according to the first embodiment. As shown in FIG. 3, the data storage 24 includes a count information storage 24a, a coincidence list storage 24b, a spatial position information storage 24c, a gradation width storage 24d, and a PET image storage 24e. The data storage 24 is, for example, a semiconductor memory device, such as a random access memory (RAM) or a flash memory, a hard disk, or an optical disk.

The count information storage 24a stores the count information for each detector module 14 which is collected by the count information collecting unit 15. Specifically, the count information storage 24a stores the count information for each detector module 14 which is transmitted from the count information collecting unit 15. The count information stored in the count information storage 24a is used in the process of the coincidence list generating unit 25. In addition, the count information stored in the count information storage 24a may be deleted after it is used in the process of the coincidence list generating unit 25 or it may be stored for a predetermined period of time.

As described above, the PET apparatus 100 according to the first embodiment generates the PET image in real time and displays the PET image in real time during the capture of the PET image. Whenever the count information is collected during an imaging operation, the count information collecting unit 15 instantly transmits the collected count information to the console 20. Therefore, the count information storage 24a sequentially stores the count information sequentially transmitted from the count information collecting unit 15.

FIG. 4 is a diagram illustrating an example of the count information stored in the count information storage 24a according to the first embodiment. As shown in FIG. 4, the count information storage 24a stores the scintillator number (P), the energy value (E), and the detection time (T) so as to be associated with a module ID for identifying the detector module 14. FIG. 4 shows all of the count information that is collected during an imaging operation and is stored in the count information storage 24a. However, as described above, since the count information storage 24a sequentially stores the count information sequentially transmitted from the count information collecting unit 15, the count information shown in FIG. 4 is sequentially stored.

The coincidence list storage 24b stores the coincidence list generated by the coincidence list generating unit 25. Specifically, the coincidence list generating unit 25 stores the coincidence list in the coincidence list storage 24b. The coincidence list stored in the coincidence list storage 24b is used in the process of the image generating unit 26. The coincidence list stored in the coincidence list storage 24b may be deleted after it is used in the process of the image generating unit 26, or it may be stored for a predetermined period of time.

As described above, the count information sequentially collected by the count information collecting unit 15 is sequentially stored in the count information storage 24a. Therefore, the coincidence list generating unit 25 sequentially generates a coincidence list and the coincidence list storage 24b sequentially stores the coincidence list sequentially generated by the coincidence list generating unit 25, which will be described below.

FIG. 5 is a diagram illustrating an example of the coincidence list stored in the coincidence list storage 24b according to the first embodiment. As shown in FIG. 5, the coincidence list storage 24b stores a combination of count information items so as to be associated with a coincidence number indicating the order in which the coincidence list is generated in time series.

The spatial position information storage 24c stores the spatial position information of the positrons estimated by a spatial position estimating unit 26a, which will be described below. Specifically, the spatial position estimating unit 26a stores the spatial position information of the positrons in the spatial position information storage 24c. The spatial position information stored in the spatial position information storage 24c is used in the process of a pixel value allocating unit 26b or a designated image generating unit 26d, which will be described below. In the first embodiment, in principle, the spatial position information stored in the spatial position information storage 24c is stored for a predetermined period of time in order to correspond to the subsequent imaging process.

As described above, the coincidence list sequentially generated by the coincidence list generating unit 25 is sequentially stored in the coincidence list storage 24b. Therefore, the spatial position estimating unit 26a sequentially estimates the spatial position and the spatial position information storage 24c sequentially stores the spatial position information sequentially stored by the spatial position estimating unit 26a, which will be described below.

FIG. 6 is a diagram illustrating an example of the spatial position information stored in the spatial position information storage 24c according to the first embodiment. As shown in FIG. 6, the spatial position information storage 24c stores the spatial position of the positron and the detection time so as to be associated with a count number indicating the order in which the coincidence list is generated in time series. As shown in FIG. 6, the spatial position of the positron is represented by, for example, a combination of the x-coordinate, the y-coordinate, and the z-coordinate.

The gradation width storage 24d stores the gradation width of the image used to generate the PET image. Specifically, the gradation width storage 24d stores the gradation width of the image that is input by the user of the PET apparatus 100 in advance. The gradation width of the image stored in the gradation width storage 24d is used in the process of a pixel value allocating unit 26b, which will be described below.

FIG. 7 is a diagram illustrating an example of the gradation width of the image stored in the gradation width storage 24d according to the first embodiment. As shown in FIG. 7, the gradation width storage 24d stores the gradation width of the image so as to be associated with the temporal resolution of the detector module 14.

As described above, a plurality of detector modules 14 is arranged in the gantry 10. Therefore, it is also considered that the temporal resolutions of the detector modules 14 are not equal to each other. Therefore, in the first embodiment, it is assumed that, before an imaging operation, timing calibration is performed using the known technique to make the temporal resolutions of all of the detector modules 14 equal to each other.

The PET image storage 24e stores the PET image generated by the pixel value allocating unit 26b or the designated image generating unit 26d, which will be described. Specifically, the pixel value allocating unit 26b or the designated image generating unit 26d stores the PET image in the PET image storage 24e. The PET image stored in the PET image storage 24e is displayed on the display 22 by the system control unit 27.

Returning to FIG. 1, the coincidence list generating unit 25 generates the coincidence list using the count information collected by the count information collecting unit 15. Specifically, the coincidence list generating unit 25 sequentially reads the count information that is sequentially stored in the count information storage 24a and searches for a combination of the count information items in which a pair of gamma rays emitted from the positron is counted at the same time on the basis of the energy value and the detection time. In addition, the coincidence list generating unit 25 generates the searched combination of the count information items as the coincidence list and stores the generated coincidence list in the coincidence list storage 24b.

For example, the coincidence list generating unit 25 generates the coincidence list on the basis of the coincidence list generation conditions input by the operator. The coincidence list generation conditions include an energy window width and a time window width. For example, the coincidence list generating unit 25 generates the coincidence list on the basis of an energy window width of "350 keV to 550 keV" and a time window width of "600 picoseconds."

For example, the coincidence list generating unit 25 refers to the energy value (E) and the detection time (T) shown in FIG. 4 with reference to the count information storage 24a. Then, the coincidence list generating unit 25 searches a combination of the count information items in which the difference between the detection times (T) is within a time window width of "600 picoseconds" and the energy value (E) is within an energy window width of "350 keV to 550 keV" from the detector modules 14. When searching for "P11, E11, T11" and "P22, E22, T22" as combinations satisfying the coincidence list generation conditions, the coincidence list generating unit 25 generates a coincidence list and stores the generated coincidence list in the coincidence list storage 24b, as shown in FIG. 5.

The operator may add parameters for performing random correction for excluding accidental coincidence, scattering correction for excluding that the count information of a scattered gamma ray is generated as the coincidence list, sensitivity correction for correcting the difference in sensitivity between the detector modules 14, or attenuation correction for correcting the energy value of the gamma ray attenuated in the subject P to the coincidence list generation conditions, in addition to the energy window width and the time window width.

Returning to FIG. 1, the image generating unit 26 will be described. As described above, the PET apparatus 100 according to the first embodiment does not generate a PET image with reconstruction using a back projection process, but generates a PET image by allocating pixel values to pixels corresponding to a gradation width, which is determined by the temporal resolution of the detector module 14, around the spatial position of the positron estimated on an LOR. This function is implemented by the process of the image generating unit 26.

Figure 8:
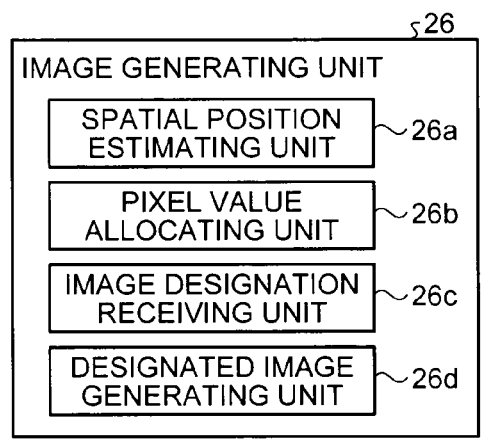
FIG. 8 is a diagram illustrating an image generating unit according to the first embodiment.

FIG. 8 is a diagram illustrating the image generating unit 26 according to the first embodiment. As shown in FIG. 8, the image generating unit 26 includes the spatial position estimating unit 26a, the pixel value allocating unit 26b, an image designation receiving unit 26c, and the designated image generating unit 26d.

The spatial position estimating unit 26a estimates the spatial position of the positron on the LOR linking a set of detector modules 14 that detect a pair of gamma rays emitted from the positron. Specifically, the spatial position estimating unit 26a sequentially reads the coincidence list sequentially stored in the coincidence list storage 24b and estimates the spatial position of the positron on the basis of the spatial position of a set of detector modules 14 specified from the scintillator number and a set of detection times. The spatial position estimating unit 26a has a TOF function, calculates the difference between the detection times from a set of detection times, and estimates the spatial position of the positron on the basis of the calculated time difference. In addition, after the spatial position is estimated, the spatial position estimating unit 26a generates spatial position information and sequentially stores the generated spatial position information in the spatial position information storage 24c.

Figure 9A:
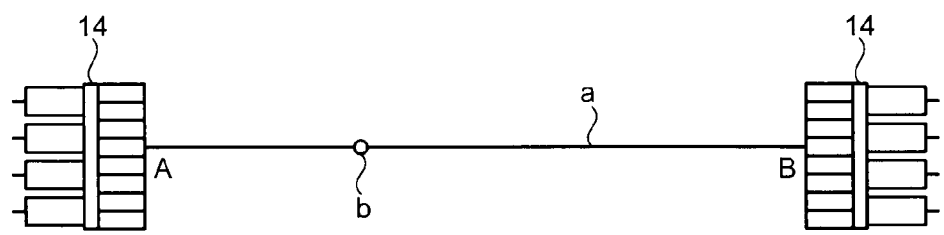
FIG. 9A is a diagram illustrating the spatial position of a positron and the allocation of a pixel value.
Figure 9B:
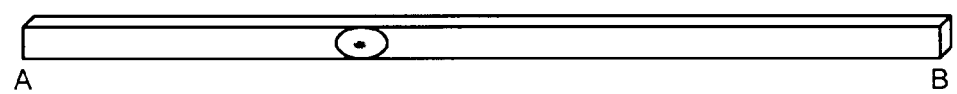
FIG. 9B is a diagram illustrating the spatial position of the positron and the allocation of the pixel value.
Figure 9C:
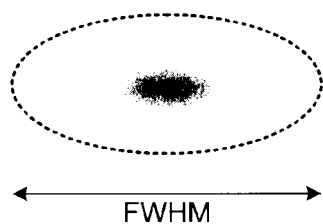
FIG. 9C is a diagram illustrating the spatial position of the positron and the allocation of the pixel value.

FIGS. 9A to 9C are diagrams illustrating the spatial position of the positron and the pixel value. As shown in FIG. 9A, a pair of gamma rays emitted from the positron is detected by a set of detector modules 14. The LOR is a line a linking a set of detector modules 14 that detect a pair of gamma rays. The spatial position estimating unit 26a calculates the difference between the detection times from a set of detection times and estimates the spatial position b of the positron on the basis of the calculated time difference. As shown in FIG. 6, the spatial position b of the positron is represented by, for example, a combination of the x-coordinate, the y-coordinate, and the z-coordinate.

The spatial position estimating unit 26a according to the first embodiment generates a combination of the count number indicating the order in which the coincidence list is generated in time series, the spatial position of the positron, and the detection time as the spatial position information. The spatial position estimating unit 26a uses the coincidence number read from the coincidence list storage 24b as the count number included in the spatial position information. In addition, the spatial position estimating unit 26a uses, for example, the earlier detection time of a set of detection times read from the coincidence list storage 24b or the average value of a set of detection times as the detection time included in the spatial position information. The spatial position estimating unit 26a may use a set of detection times as the detection time included in the spatial position information.

Returning to FIG. 8, the pixel value allocating unit 26b allocates pixel values to pixels corresponding to the gradation width which is stored in the gradation width storage 24d around the spatial position of the positron estimated by the spatial position estimating unit 26a, thereby generating a PET image. In this way, the spatial resolution corresponding to the temporal resolution of the detector module 14 is reflected on the LOR linking a set of detector modules 14.

Specifically, the pixel value allocating unit 26b sequentially reads the spatial position information sequentially stored in the spatial position information storage 24c. In addition, the pixel value allocating unit 26b acquires the gradation width which is stored so as to be associated with the temporal resolution of the detector module 14 with reference to the gradation width storage 24d. Then, the pixel value allocating unit 26b allocates pixel values to pixels corresponding to the acquired gradation width around the spatial position which is included in the spatial position information, thereby generating a PET image. Then, the pixel value allocating unit 26b sequentially stores the generated PET image in the PET image storage 24e.

Figure 10A:
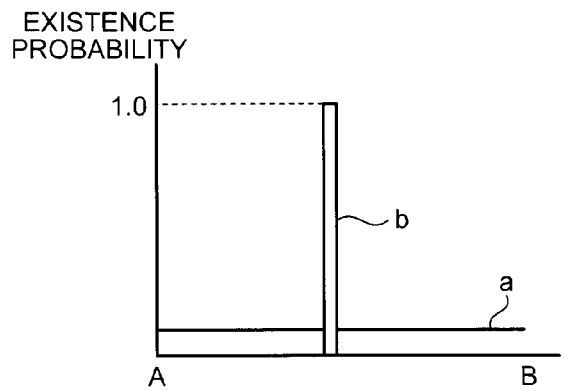
FIG. 10A is a diagram illustrating the relationship between a temporal resolution and a gradation width.
Figure 10B:
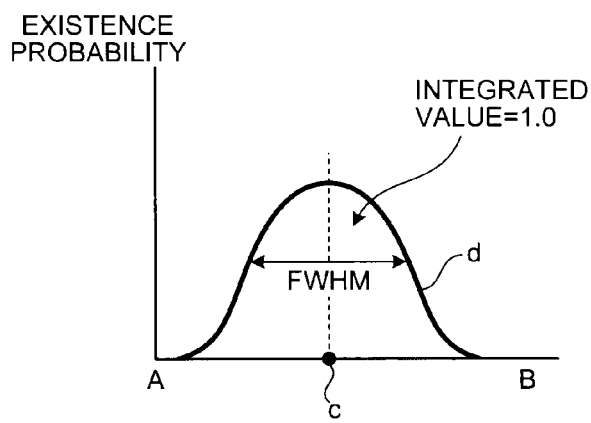
FIG. 10B is a diagram illustrating the relationship between the temporal resolution and the gradation width.

FIGS. 10A and 10B are diagrams illustrating the relationship between the temporal resolution and the gradation width. If the PET apparatus does not have the TOF function, the PET apparatus assumes that the positrons are present on the LOR with equal probability. This is represented by a straight line a in FIG. 10A. If the PET apparatus has the TOF function and the temporal resolution is infinite, the PET apparatus supposes that the positron is present at one point on the LOR. This is represented by a bar graph b in FIG. 10A, in which existence probability is 1.0.

Therefore, when the temporal resolution is relatively high, as shown in FIG. 10B, the PET apparatus 100 according to the first embodiment allocates pixel values to the pixels corresponding to the gradation width which is determined by the temporal resolution of the detector module 14 around the spatial position c of the positron which is estimated on the LOR, thereby generating a PET image. When the gradation distribution of the image is a mountain-shaped function d shown in FIG. 10B, the gradation width is, for example, the full width at half maximum (FWHM) of the function. The integrated value of the existence probability is 1.0.

As shown in FIG. 7, the gradation width storage 24d according to the first embodiment stores the gradation width of the image in advance so as to be associated with the temporal resolution of the detector module 14. As described above, in the first embodiment, before an imaging operation, timing calibration is performed using the known technique to measure the average temporal resolution of all of the detector modules 14 and the measured average temporal resolution is used as the system temporal resolution. For example, assuming that the system temporal resolution is "200 picoseconds," the temporal resolution of all of the measured coincidences is "200 picoseconds."

In this case, the pixel value allocating unit 26b acquires a gradation width (FWHM) of "60 mm" which is stored so as to be associated with a temporal resolution (FWHM) of "200 picoseconds" of the detector module 14, with reference to the gradation width storage 24d. Then, the pixel value allocating unit 26b allocates "points" indicating that there are pixel values to pixels corresponding to the acquired gradation width of "60 mm" around the spatial position which is represented by a combination of the x-coordinate, the y-coordinate, and the z-coordinate, thereby generating the PET image.

For example, as shown in FIGS. 9B and 9C, the pixel values are allocated in an elliptical shape around the estimated spatial position such that the LOR direction is the gradation width. In addition, as shown in FIGS. 9B and 9C, the pixel values are allocated such that the brightness of the spatial position is high and the brightness is reduced as the distance from the spatial position increases. This process can be performed in a short time, unlike reconstruction using the back projection process.

Returning to FIG. 8, the image designation receiving unit 26c receives an instruction to designate the generation conditions of the PET image. Specifically, the image designation receiving unit 26c receives at least one of the detection time and the space coordinates as the generation conditions of the PET image designated by the operator of the PET apparatus 100. In addition, the image designation receiving unit 26c transmits the received designated conditions to the designated image generating unit 26d.

The designated image generating unit 26d generates a PET image on the basis of the designated conditions received by the image designation receiving unit 26c. Specifically, when receiving the designated conditions from the image designation receiving unit 26c, the designated image generating unit 26d acquires the spatial position information required to generate a PET image using the received designated condition with reference to the spatial position information storage 24c. Then, the designated image generating unit 26d generates a PET image using the acquired spatial position information.

For example, when receiving the detection times "$t_x$ to $t_y$" as the designated conditions, the designated image generating unit 26d acquires only the spatial position information in which the detection time is in the range of "$t_x$ to $t_y$" with reference to the spatial position information storage 24c. Then, the designated image generating unit 26d generates the PET image using the same method as that used by the pixel value allocating unit 26b. That is, the designated image generating unit 26d acquires the gradation width which is stored so as to be associated with the temporal resolution of the detector module 14 with reference to the gradation width storage 24d. Then, the designated image generating unit 26d allocates pixel values to the pixels corresponding to the acquired gradation width around the spatial position which is included in the spatial position information, thereby generating a PET image. Then, the designated image generating unit 26d stores the generated PET image in the PET image storage 24e. When the space coordinates are designated as the generation conditions, similarly, the designated image generating unit 26d acquires only the spatial position information of the space coordinates with reference to the spatial position information storage 24c.

As such, in the PET apparatus 100 according to the first embodiment, for example, after an imaging operation, the image designation receiving unit 26c receives the designated generation conditions of the PET image and the designated image generating unit 26d generates a new PET image on the basis of the received designated conditions.

That is, the PET image generated by the pixel value allocating unit 26b is displayed in real time during an imaging operation. However, the PET image generated by the designated image generating unit 26d is mainly displayed after an imaging operation. For example, after an imaging operation, the doctor designates only the time width of interest, only the image region of interest, or both the time width of interest and the image region of interest. Then, the designated image generating unit 26d generates a PET image corresponding to the designated conditions.

For example, it is assumed that an imaging operation is performed for one hour and the spatial position information corresponding to one hour is stored in the spatial position information storage 24c. In this case, it is considered that, after the imaging operation, the doctor wants to examine, for example, the test time of a medicine or a time activity curve and observe only the PET image captured at a given time. In this case, the spatial position information storage 24c according to the first embodiment stores all of the spatial positions of the positrons estimated during the imaging operation and the examination time so as to be associated with each other. Therefore, even when the doctor wants to observe only the PET image captured at a given time after the imaging operation, the PET apparatus 100 according to the first embodiment can flexibly extract the spatial position information corresponding to the given time and generate a desired PET image after the imaging operation. When the image region is designated, the same process as that when the time is designated is performed.

The system control unit 27 controls the gantry 10 and the console 20 to control the overall operation of the PET apparatus 100. For example, the system control unit 27 controls the imaging operation of the PET apparatus 100. In addition, for example, the system control unit 27 controls the count information collecting process of the count information collecting unit 15 or the coincidence list generating process of the coincidence list generating unit 25. Further, for example, the system control unit 27 controls the image generating process of the image generating unit 26.

Furthermore, for example, the system control unit 27 controls the display of the PET image stored in the data storage 24. For example, whenever the pixel value allocating unit 26b sequentially stores the PET image in the data storage 24, the system control unit 27 sequentially reads the PET image and sequentially displays the read PET image on the display 22. In this way, during the capture of the PET image, the PET image is displayed in real time. For example, when the designated image generating unit 26d stores the PET image in the data storage 24, the system control unit 27 reads the PET image and displays the read PET image on the display 22.

Figure 11:
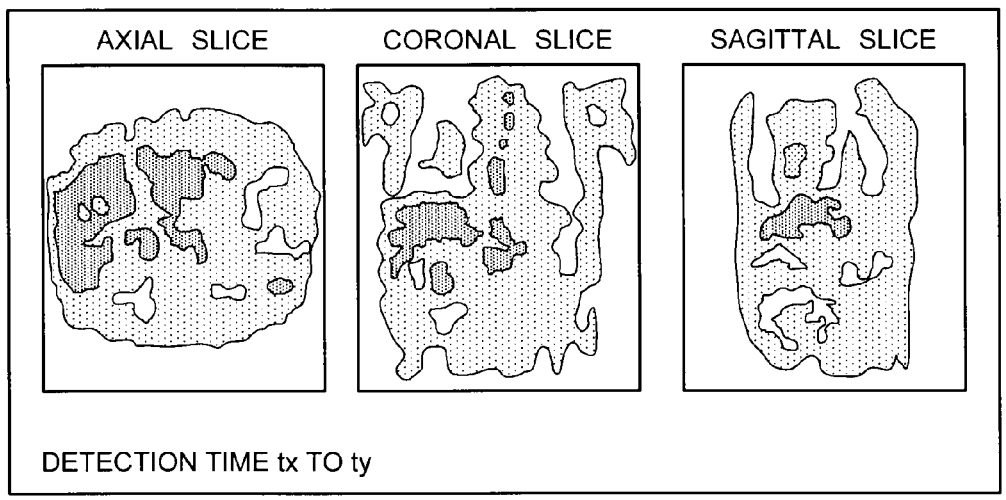
FIG. 11 is a diagram illustrating the display of the generated PET image.

FIG. 11 is a diagram illustrating the display of the generated PET image. For example, when receiving the display direction (for example, the two-dimensional direction, such as the axial, coronal, and sagittal directions) of the PET image designated by the operator of the PET apparatus 100, the system control unit 27 displays the PET image generated by the pixel value allocating unit 26b or the designated image generating unit 26d on the display 22 in the received display direction. For example, when receiving an instruction to display the PET images in all of the display directions, that is, in the axial, coronal, and sagittal directions, the system control unit 27 displays all of the PET images on one screen in the axial, coronal, and sagittal directions, as shown in FIG. 11.

For example, each of the coincidence list generating unit 25, the image generating unit 26, and the system control unit 27 is implemented by an integrated circuit, such as an application specific integrated circuit (ASIC) or a field programmable gate array (FPGA), or an electronic circuit, such as a central processing unit (CPU) or a micro processing unit (MPU).

Next, the process of the PET apparatus 100 according to the first embodiment will be described with reference to FIGS. 12 and 13. FIG. 12 is a flowchart illustrating a process of displaying the PET image in real time. FIG. 13 is a flowchart illustrating a process of displaying the captured PET image.

As shown in FIG. 12, in the PET apparatus 100 according to the first embodiment, when an imaging operation starts (Step S101: Yes), the count information collecting unit 15 sequentially collects count information (Step S102) and the coincidence list generating unit 25 sequentially generates a coincidence list (Step S103).

Then, the spatial position estimating unit 26a sequentially estimates the spatial position of the positron (Step S104). The pixel value allocating unit 26b allocates pixel values to the pixels corresponding to the gradation width stored in the gradation width storage 24d around the spatial position of the positron estimated by the spatial position estimating unit 26a, thereby sequentially generating a PET image (Step S105).

Then, the system control unit 27 sequentially displays the PET image sequentially generated by the pixel value allocating unit 26b on the display 22 (Step S106). A series of processes from Steps S102 to S106 is repeatedly performed until the imaging operation ends and it is possible to display the PET image in real time during the imaging operation.

Then, as shown in FIG. 13, in the PET apparatus 100 according to the first embodiment, after the imaging operation, when the image designation receiving unit 26c receives a designated time width (Step S201: Yes), the designated image generating unit 26d acquires spatial position information corresponding to the designated time width (Step S202).

Then, the designated image generating unit 26d allocates pixel values to the pixels corresponding to the gradation width stored in the gradation width storage 24d around the spatial position included in the acquired spatial position information, thereby sequentially generating a PET image (Step S203). Then, the system control unit 27 displays the PET image generated by the designated image generating unit 26d on the display 22 (Step S204).

As described above, the PET apparatus 100 according to the first embodiment includes the gradation width storage 24d. The gradation width storage 24d stores the gradation width of the image which is determined by the temporal resolution of the detector module 14 detecting gamma rays. In addition, the PET apparatus 100 includes the spatial position estimating unit 26a and the pixel value allocating unit 26b. The spatial position estimating unit 26a estimates the spatial position of the positron on the LOR linking a set of detector modules 14 that detect a pair of gamma rays emitted from the positron, on the basis of the spatial positions of the set of detector modules 14 and a set of detection times when the set of detector modules 14 detect the pair of gamma rays. The pixel value allocating unit 26b allocates pixel values to the pixels corresponding to the gradation width stored in the gradation width storage 24d around the spatial position estimated by the spatial position estimating unit 26a such that the spatial resolution corresponding to the temporal resolution is reflected on the LOR linking the set of detector modules 14, thereby generating an image. The PET apparatus 100 according to the first embodiment displays the PET image on the display 22 in a predetermined two-dimensional direction.

In this way, according to the first embodiment, it is possible to reduce the time required to generate the PET image. For example, it is possible to display the PET image in real time during an imaging operation. In addition, for example, it is possible to display the PET image during a medical treatment.

The PET apparatus 100 according to the first embodiment includes the spatial position information storage 24c. The spatial position information storage 24c stores the spatial position of the positron estimated by the spatial position estimating unit 26a and the detection time when the detector module 14 detects the positron so as to be associated with each other. In addition, the PET apparatus 100 includes the image designation receiving unit 26c and the designated image generating unit 26d. The image designation receiving unit 26c receives at least one of the spatial position and the detection time as the designated generation conditions of the PET image. The designated image generating unit 26d acquires the spatial position required to generate the PET image using the designated conditions received by the image designation receiving unit 26c with reference to the spatial position information storage 24c, and allocates pixel values to the pixels corresponding to the gradation width stored in the gradation width storage 24d around the acquired spatial position, thereby generating an image.

In this way, according to the first embodiment, for example, even when the doctor wants to observe only the PET image captured at a given time (or a given image region) after the imaging operation, it is possible to flexibly extract the spatial position information corresponding to the given time (or the given image region) and generate a desired PET image after the imaging operation. The term "flexibility" is different from that depending on the time interval which is collected during an imaging operation, such as the dynamic imaging operation according to the related art. That is, both the time and the image region may be arbitrarily designated.

The disclosed technique may be implemented by various embodiments other than the above-described embodiment.

First, in the first embodiment, it is assumed that, before an imaging operation, timing calibration is performed using the known technique to make the temporal resolutions of all of the detector modules 14 equal to each other. However, the embodiment is not limited thereto. For example, when the temporal resolutions of the detector modules 14 are different from each other, the image generating unit 26 may generate images using the gradation width corresponding to the temporal resolution of each of the detector modules 14.

For example, the PET apparatus 100 performs timing calibration before an imaging operation, measures the temporal resolution of each of the detector modules 14, and stores the measurement result in the storage. Then, when acquiring the temporal resolution of each of a set of the detector modules 14 with reference to the storage, the pixel value allocating unit 26b refers to the gradation width storage 24d using, for example, the minimum temporal resolution (or the average value). Then, the pixel value allocating unit 26b acquires the gradation width and allocates pixel values to the pixels corresponding to the acquired gradation width around the spatial position included in the spatial position information, thereby generating a PET image.

In the first embodiment, the PET apparatus 100 includes only the image generating unit 26 and does not perform reconstruction using the back projection process. However, the embodiment is not limited thereto. For example, the PET apparatus 100 may further include an image reconstruction unit that performs reconstruction using the back projection process and may select, for example, a process of generating an image using the image generating unit 26 or a process of reconstructing an image using the image reconstruction unit, according to the temporal resolution. For example, when the temporal resolution cannot reach 200 picoseconds, the PET apparatus 100 may select the process of reconstructing an image using the image reconstruction unit.

In the first embodiment, the PET apparatus 100 has the structure shown in FIG. 1, but the embodiment is not limited thereto. For example, the count information collecting unit 15 may be provided in the console 20. On the contrary, the coincidence list generating unit 25 may be provided in the gantry 10. In addition, various kinds of data stored in the data storage 24 may be provided in the gantry 10 or the console 20.

In the first embodiment, the PET apparatus 100 is given as an example, but the embodiment is not limited thereto. The technique according to the first embodiment can be similarly applied to a radiation therapy apparatus.

The radiation therapy apparatus includes an emitting unit that emits a heavy particle beam. The radiation therapy apparatus emits the heavy particle beam to a tumor cell of the subject. In this case, an accelerator is used to adjust the energy of particles such that the particles are stopped in the tumor cell of the subject.

When the energy is equal to or more than "511×2 keV," the heavy particle beam generates a pair of an electron and a positron while it travels. The generated positron is coupled to the neighboring electron to be extinguished. As a result, annihilation gamma rays are emitted.

Therefore, in recent years, a radiation therapy apparatus that also serves as a PET apparatus has appeared. The radiation therapy apparatus detects the emitted annihilation gamma rays and generates a PET image. That is, the radiation therapy apparatus can display the PET image while emitting the heavy particle beam. The doctor can monitor whether the heavy particle beam is emitted to the tumor cell during a medical treatment.

A PET apparatus included in the radiation therapy apparatus includes, for example, a set of flat detectors and the set of detectors are provided so as to face each other with the subject interposed therebetween.

The PET apparatus has the same function as the PET apparatus 100.

Figure 14:
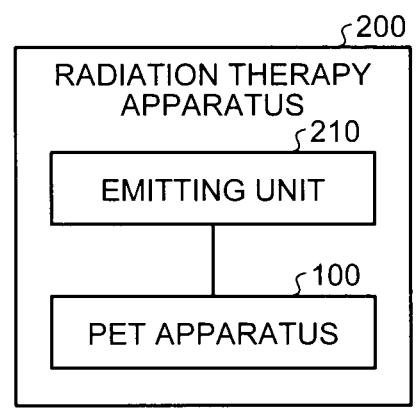
FIG. 14 is a block diagram illustrating the structure of a radiation therapy apparatus according to another embodiment.

FIG. 14 is a block diagram illustrating the structure of a radiation therapy apparatus according to another embodiment. That is, as shown in FIG. 14, a radiation therapy apparatus 200 includes an emitting unit 210 that emits a heavy particle beam. In addition, the radiation therapy apparatus 200 includes a PET apparatus that has the same structure as the PET apparatus 100. In this case, for example, a set of flat detectors are provided so as to face each other with the subject interposed therebetween. The set of detectors detect a pair of radiations that is emitted with the energy emission of the heavy particle beam emitted from the emitting unit 210. Specifically, the radiation therapy apparatus 200 includes, for example, the gradation width storage 24d, the spatial position estimating unit 26a, the pixel value allocating unit 26b, the image designation receiving unit 26c, the designated image generating unit 26d, and the system control unit 27.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus comprising:
    a gradation width storage configured to store a gradation width of an image determined by a temporal resolution of a detector which detects radiation;
    an estimating unit configured to estimate a spatial position of a positron on a line linking a set of detectors which detect a pair of radiations emitted from the positron, on a basis of the spatial position of the set of detectors and a set of detection times when the set of detectors detect the pair of radiations;
    an image generating unit configured to allocate pixel values to pixels corresponding to the gradation width which is stored in the gradation width storage around the spatial position estimated by the estimating unit such that a spatial resolution corresponding to the temporal resolution is reflected on the line linking the set of detectors, thereby generating an image without performing a back projection reconstruction process;
    a display control unit configured to sequentially display, on a display, the image sequentially generated by the image generating unit, to display the image in real time during an imaging operation; and
    an imaging reconstruction unit configured to perform reconstruction using a back projection process, wherein the nuclear medicine imaging apparatus selects one of a process of generating an image using the image generating unit and a process of reconstructing an image using the image reconstruction unit.

2. The nuclear medicine imaging apparatus according to claim 1, further comprising:
    a spatial position storage configured to store the spatial position of the positron estimated by the estimating unit and the detection time when the positron is detected by the detector so as to be associated with each other;
    a designation receiving unit configured to receive at least one of the spatial position and the detection time as designated conditions of an image to be generated; and
    a designated image generating unit configured to acquire a spatial position required to generate the image using the designated conditions received by the designation receiving unit with reference to the spatial position storage and allocates pixel values to pixels corresponding to the gradation width which is stored in the gradation width storage around the acquired spatial position, thereby generating an image without performing a back projection reconstruction process, wherein the display control unit is configured to sequentially display, on the display, the image sequentially generated by the designated image generating unit, to display the image in real time during the imaging operation.

3. The nuclear medicine imaging apparatus according to claim 2, wherein
the display control unit is configured to display the image on the display in a predetermined two-dimensional direction.

4. The nuclear medicine imaging apparatus according to claim 1, wherein the display control unit is configured to display the image on the display in a predetermined two-dimensional direction.

5. The nuclear medicine imaging apparatus according to claim 1, wherein
the pixel values are allocated in an elliptical shape around the spatial position estimated by the estimating unit.

6. A radiation therapy apparatus comprising:
an emitting unit configured to emit a heavy particle beam;
a set of detectors configured to detect a pair of radiations which is emitted with an energy emission of the heavy particle beam emitted from the emitting unit;
a gradation width storage configured to store a gradation width of an image determined by a temporal resolution of the set of detectors;
an estimating unit configured to estimate a spatial position of a positron on a line linking the set of detectors, on a basis of the spatial position of the set of detectors and a set of detection times when the set of detectors detect the pair of radiations;
an image generating unit configured to allocate pixel values to pixels corresponding to the gradation width which is stored in the gradation width storage around the spatial position estimated by the estimating unit such that a spatial resolution corresponding to the temporal resolution is reflected on the line linking the set of detectors, thereby generating an image without performing a back projection reconstruction process;
a display control unit configured to sequentially display, on a display, the image sequentially generated by the image generating unit, to display the image in real time during an imaging operation; and
an imaging reconstruction unit configured to perform reconstruction using a back projection process, wherein
the radiation therapy apparatus selects one of a process of generating an image using the image generating unit and a process of reconstructing an image using the image reconstruction unit.

7. The radiation therapy apparatus according to claim 6, further comprising:
a spatial position storage configured to store the spatial position of the positron estimated by the estimating unit and the detection time when the positron is detected by the detector so as to be associated with each other;
a designation receiving unit configured to receive at least one of the spatial position and the detection time as designated conditions of an image to be generated; and
a designated image generating unit configured to acquire a spatial position required to generate the image using the designated conditions received by the designation receiving unit with reference to the spatial position storage and allocates pixel values to pixels corresponding to the gradation width which is stored in the gradation width storage around the acquired spatial position, thereby generating an image without performing a back projection reconstruction process, wherein
the display control unit is configured to sequentially display, on the display, the image sequentially generated by the designated image generating unit, to display the image in real time during the imaging operation.

8. The radiation therapy apparatus according to claim 7, wherein
the display control unit is configured to display the image on the display in a predetermined two-dimensional direction.

9. The radiation therapy apparatus according to claim 6, wherein
the display control unit is configured to display the image on the display in a predetermined two-dimensional direction.

* * * * *